US011852686B2

(12) United States Patent
Li et al.

(10) Patent No.: US 11,852,686 B2
(45) Date of Patent: Dec. 26, 2023

(54) FAULT DIAGNOSIS METHOD AND SYSTEM FOR HIGH-VOLTAGE GENERATOR

(71) Applicant: Delta Electronics (Shanghai) Co., Ltd., Shanghai (CN)

(72) Inventors: Linchun Li, Shanghai (CN); Dezhi Jiao, Shanghai (CN); Jinfa Zhang, Shanghai (CN)

(73) Assignee: DELTA ELECTRONICS (SHANGHAI) CO., LTD., Shanghai (CN)

( * ) Notice: Subject to any disclaimer, the term of this patent is extended or adjusted under 35 U.S.C. 154(b) by 357 days.

(21) Appl. No.: 17/169,559

(22) Filed: Feb. 8, 2021

(65) Prior Publication Data

US 2021/0293885 A1    Sep. 23, 2021

(30) Foreign Application Priority Data

Mar. 18, 2020    (CN) .......................... 202010192070.7

(51) Int. Cl.
*G01R 31/34* (2020.01)
*G01R 31/08* (2020.01)
*A61B 6/00* (2006.01)

(52) U.S. Cl.
CPC ......... *G01R 31/343* (2013.01); *G01R 31/088* (2013.01); *A61B 6/586* (2013.01)

(58) Field of Classification Search
CPC .... G01R 31/343; G01R 31/088; G01R 31/12; G01R 31/56; G01R 31/40; A61B 6/586; G06F 1/30; G06F 18/24323
See application file for complete search history.

(56) References Cited

U.S. PATENT DOCUMENTS

2016/0169959 A1* 6/2016 Li .................. G01R 31/52
324/552
2017/0124325 A1   5/2017 Alme et al.
(Continued)

FOREIGN PATENT DOCUMENTS

CN    101819604 A    9/2010
CN    103902816 A    7/2014
(Continued)

OTHER PUBLICATIONS

Office Action of CN Application No. 202010192070.7 dated Aug. 8, 2023.

*Primary Examiner* — Farhana A Hoque
(74) *Attorney, Agent, or Firm* — CKC & Partners Co., LLC (57) ABSTRACT

The present disclosure relate to a fault diagnosis method, including: collecting at least one set of original data of the high voltage generator during operation, each condition attribute in a condition attribute set corresponding to one piece of original data; pre-processing the original data to obtain pre-processed data and generating a decision table; performing an attribute reduction based on the decision table to obtain a reduced condition attribute set and a reduced decision table; generating a decision tree model according to the reduced decision table; generating a decision forest model according to at least one decision tree model; obtaining a fault type and a fault level according to the decision forest model; determining an acceptable level of the fault according to the fault level and a frequency of occurrence of the same type of fault, and sending the fault type and the acceptable level to the display terminal.

14 Claims, 5 Drawing Sheets

(56) References Cited

U.S. PATENT DOCUMENTS

2019/0012605 A1\* 1/2019 Rajagopal .............. G06N 20/00
2019/0220595 A1 7/2019 Gehweiler et al.

FOREIGN PATENT DOCUMENTS

| CN | 106202886 A | 12/2016 |
| CN | 107679583 A | 2/2018 |
| CN | 108053148 A | 5/2018 |
| CN | 108335013 A | 7/2018 |
| CN | 109146228 A | 1/2019 |
| CN | 109298330 A | 2/2019 |
| CN | 109543210 A | 3/2019 |
| CN | 109635873 A | 4/2019 |
| CN | 109670611 A | 4/2019 |
| CN | 110414567 A | 11/2019 |

\* cited by examiner

FAULT DIAGNOSIS METHOD AND SYSTEM FOR HIGH-VOLTAGE GENERATOR

CROSS-REFERENCE TO RELATED APPLICATIONS

This application claims priority to Chinese Patent Application No. 202010192070.7, filed on Mar. 18, 2020, which is incorporated herein by reference in its entirety.

TECHNICAL FIELD

Embodiments of the present disclosure relate to the field of data processing technologies, and in particular, to a fault diagnosis method and system for a high-voltage generator.

BACKGROUND

The high-voltage generator is a core of an X-ray diagnostic system. Due to its numerous high-voltage components and peripheral controllers, the system has complex connections, and thus it is necessary to diagnose in time whether the high-voltage power supply has faults to ensure a stable operation of the system.

At present, a traditional power supply fault diagnosis is performed by collecting input and output signals of the high-voltage power supply, and diagnosing based on a threshold and performing a signal processing, and after a fault is diagnosed, protection is performed by a fixed protection strategy.

However, the fault diagnosis condition of this diagnosis method is single, which makes that the high-voltage generator can only be diagnosed after a serious fault occurs, and it is impossible to locate the location and reason of the fault and provide early warning, thereby reducing an accuracy and timeliness of the fault diagnosis, and meanwhile because it does not have a learning mechanism, the diagnosis result cannot be explained.

SUMMARY

Embodiments of the present disclosure provide a fault diagnosis method and a fault diagnosis system, for a high-voltage generator, so as to solve the problems in the prior art: failure to locate the location and reason of the fault and provide an early warning, resulting in a decrease in accuracy and timeliness of the fault diagnosis, and failure to explain the diagnosis result.

A first aspect of embodiments of the present disclosure provides a fault diagnosis method for a high-voltage generator, including:

collecting at least one set of original data of the high voltage generator during operation;

pre-processing the original data to obtain pre-processed data and generating a decision table;

performing an attribute reduction based on the decision table to obtain a reduced decision table;

generating a decision tree model according to the reduced decision table;

generating a decision forest model according to at least one decision tree model;

obtaining a fault type and a fault level corresponding to a fault of the high-voltage generator according to the decision forest model; and determining an acceptable level of the fault according to the fault level and a frequency of occurrence of the same type of fault.

A second aspect of embodiments of the present disclosure provides a fault diagnosis system for a high-voltage generator, including:

a collecting and processing module, configured to collect at least one set of original data of the high voltage generator during operation, pre-process the original data to obtain pre-processed data and generate a decision table, perform an attribute reduction based on the decision table to obtain a reduced decision table;

a model building module, configured to generate a decision tree model according to the reduced decision table, and generate a decision forest model according to at least one decision tree model; and a fault determining module, configured to obtain a fault type and a fault level corresponding to a fault of the high-voltage generator according to the decision forest model;

the fault determining module is further configured to determine an acceptable level of the fault according to the fault level and a frequency of occurrence of the same type of fault.

Embodiments of the present disclosure provide a fault diagnosis method and a fault diagnosis system for a high-voltage generator, where by collecting at least one set of original data of the high voltage generator during operation, then pre-processing the original data to obtain pre-processed data and generating a decision table; performing an attribute reduction based on the decision table to obtain a reduced decision table; generating a decision tree model according to the reduced decision table; generating a decision forest model according to at least one decision tree model; obtaining a fault type and a fault level corresponding to a fault of the high-voltage generator by building the decision forest model; thereby determining an acceptable level of the fault according to the fault level and a frequency of occurrence of the same type of fault, it is possible to enable users to analyze the fault type and the acceptable level of the fault in time and take a corresponding measure to realize early warning of the fault type and the level, improving the accuracy and timeliness of fault diagnosis.

BRIEF DESCRIPTION OF THE DRAWINGS

In order to more clearly explain the technical solutions in the embodiments of the present disclosure or in the prior art, the drawings used in the descriptions of the embodiments or the prior art will be briefly introduced below. Obviously, the drawings in the following description are merely some of embodiments of the present disclosure. For those of ordinary skill in the art, other drawings can be obtained based on these drawings without creative efforts.

DETAILED DESCRIPTION OF THE EMBODIMENTS

In order to make objectives, technical solutions and advantages of the embodiments of the present disclosure clearer, the technical solutions in the embodiments of the present disclosure will be described hereunder clearly and completely with reference to the accompanying drawings in the embodiments of the present disclosure. Obviously, the described embodiments are part of embodiments of the present disclosure, rather than all embodiments of the present disclosure. All other embodiments obtained by persons of ordinary skill in the art based on the embodiments of the present disclosure without any creative effort should fall into the protection scope of the present disclosure.

Terms such as "first", "second", "third", "fourth", etc. (if present), as used in the specification and the claims as well as the described accompany drawings of the present disclosure, are used to distinguish similar objects, but not intended to describe a specific order or sequence. It will be appreciated that the data used in this way may be interchangeable under appropriate circumstances, such that the embodiments of the present disclosure described herein can be implemented in an order other than those orders illustrated or described herein, for example. Moreover, terms such as "include" and "have" and any variation thereof are intended to cover a non-exclusive inclusion, e.g., processes, methods, systems, products or devices that involve a series of steps or units are not necessarily limited to those steps or units that are clearly listed, and may include other steps or units that are not explicitly listed or inherent to these processes, methods, products or devices.

Traditional power supply fault diagnosis is done by collecting input and output signals of a high-voltage power supply, and after a fault is diagnosed based on a threshold diagnosis and a signal processing, performing a protection by a fixed protection strategy.

However, this diagnosis method usually has single fault judgment condition, which makes that a serious fault in the high-voltage generator can only be diagnosed after the fault occurs and it is unable to locate the source of the fault and perform early warning, thereby reducing the accuracy and timeliness of fault diagnosis, and meanwhile since it does not have a learning mechanism, it also cannot explain the results of the diagnosis.

In view of this defect, embodiments of the present disclosure provide a fault diagnosis method and a fault diagnosis system for a high-voltage generator, where by collecting at least one set of original data of the high voltage generator during operation, then pre-processing the original data to obtain pre-processed data and generating a decision table; performing an attribute reduction based on the decision table to obtain a reduced decision table; generating a decision tree model according to the reduced decision table; generating a decision forest model according to at least one decision tree model; obtaining a fault type and a fault level corresponding to a fault of the high-voltage generator by building the decision forest model; thereby determining an acceptable level of the fault according to the fault level and a frequency of occurrence of the same type of fault, the method may allow users to analyze the fault type and the acceptable level of the fault in time and take a corresponding measure to realize early warning of the fault types and the level. This can identify not only an actual fault but also a potential fault, improving the accuracy and timeliness of fault diagnosis.

Figure 1:
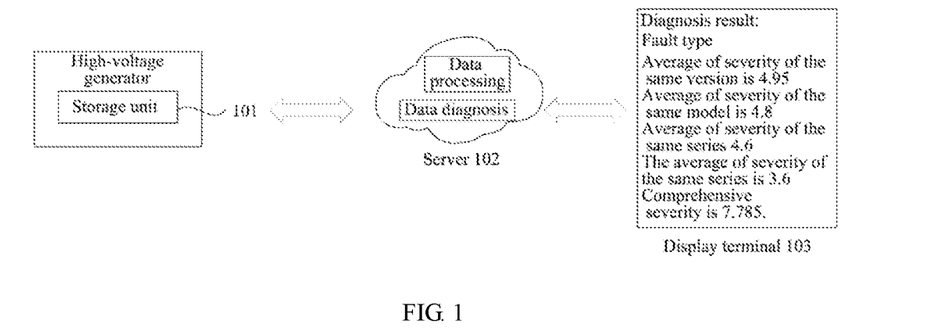
FIG. 1 is an application scenario diagram of a fault diagnosis method for a high-voltage generator according to an exemplary embodiment of the present disclosure.

FIG. 1 is an application scenario diagram of a fault diagnosis method for a high-voltage generator according to an exemplary embodiment of the present disclosure.

As shown in FIG. 1, a basic architecture of this scenario mainly includes: a storage unit 101, configured to store at least one set of original data when the high-voltage generator is operating; a server 102 and a display terminal 103;

The server includes a data processing unit and a data diagnosis unit, which are configured to perform a related processing and diagnosis on the original data to obtain a fault diagnosis result of the high-voltage generator, and send the fault diagnosis result to the display terminal, so that the user can view the fault diagnosis result through the display terminal.

The communication between a high-voltage converter and the server and between the server and the display terminal may adopt Ethernet communication, but is not limited to this.

Figure 2:
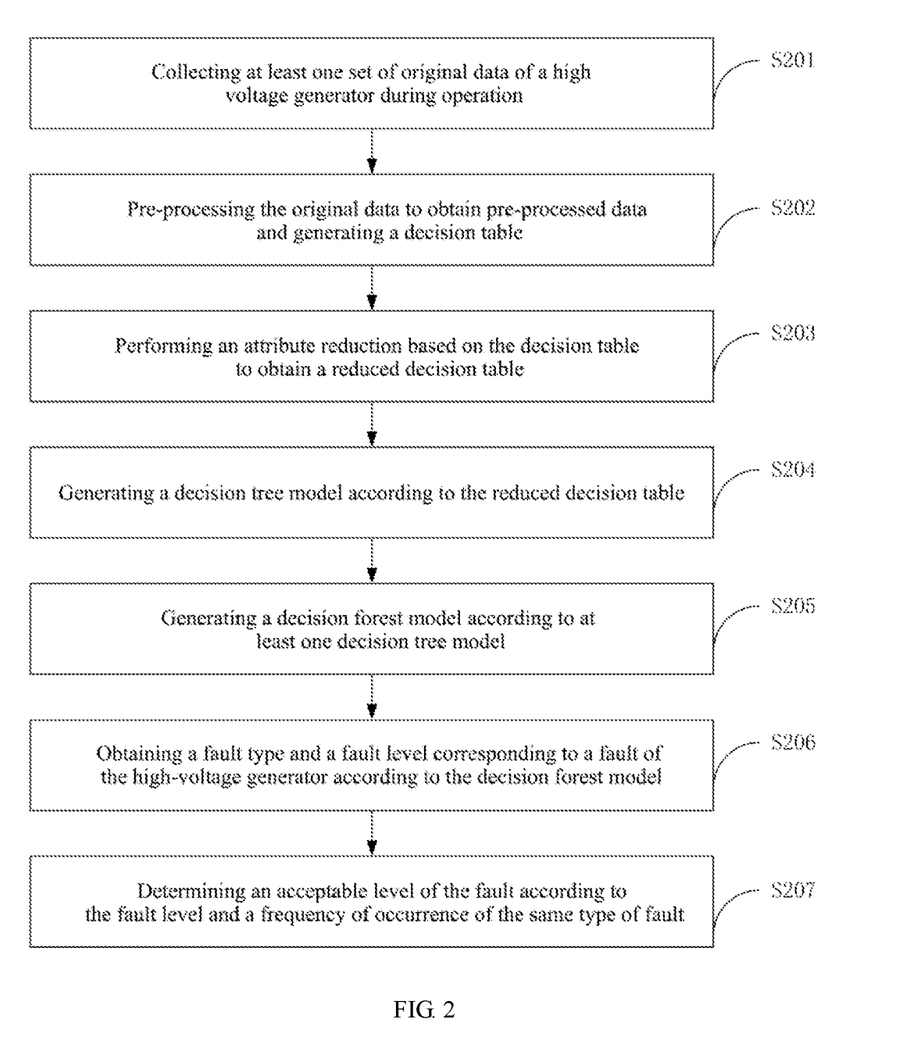
FIG. 2 is a schematic flowchart of a fault diagnosis method for a high-voltage generator according to another exemplary embodiment of the present disclosure.

FIG. 2 is a schematic flowchart of a fault diagnosis method for a high-voltage generator according to another exemplary embodiment of the present disclosure. An executive entity of the method provided by this embodiment may be a server in the embodiment shown in FIG. 1.

As shown in FIG. 2, the method provided in this embodiment may include the following steps:

S201: collecting at least one set of original data of the high voltage generator during operation.

Among them, one piece of original data in each set of original data corresponds to one condition attribute in a condition attribute set. The original data is data generated during the operation of the high-voltage generator, and each piece of original data includes data such as exposure parameters (such as voltage, current, mode, time, filament size, motor rotation speed, and other parameters); voltage and current curve; control parameters (such as control frequency, startup frequency, PI parameter, feedforward coefficient, filament reference adjustment range, burst interval time, etc.); filament current curve; temperature curve; and error codes.

Where the voltage and current curve is obtained by recording voltage and current values at intervals. For example, when the working time is less than 2 ms, it is recorded once every 100 us, and when the working time is greater than 2 ms, it is recorded once every 1 ms; the control frequency is recorded once every 100 us; the filament current curve is obtained by recording the filament current once every 20 ms; and the temperature curve is obtained by recording the temperature once every 100 ms.

Specifically, during the operation of the high-voltage generator, data is collected and generated in real time, and stored as original data in a storage unit. When the high-voltage generator stops running and communication is idle, the collected data is sent to a cloud data processing platform, for example, to a cloud server.

S202: pre-processing the original data to obtain pre-processed data and generating a decision table.

In some embodiments, some of the original data may be missing, for example, lack of exposure parameters such as voltage and current; some of the original data may include abnormal data, for example, too large voltage value; in some original data, the same type of data is represented differently. Therefore, it is necessary to pre-process all the original data.

Specifically, the original data is processed to obtain data in a unified format; the data in a unified format is discretized according to a preset standard to obtain at least one set of attribute values corresponding to the condition attribute; a decision table is generated according to the condition attributes and the pre-processed data.

S203: performing an attribute reduction based on the decision table to obtain a reduced decision table.

Where the decision table includes at least one condition attribute corresponding to at least one set of original data, and a condition attribute corresponding to each attribute value in one set of original data.

Specifically, in at least one set of original data, there may be original data that has little influence on the decision result. Therefore, an importance of the condition attribute set is calculated, and one condition attribute in the condition attribute set is removed, and an importance of a remaining condition attribute set is calculated, and if the importance of the remaining condition attribute set is the same as the importance of the original condition attribute set, the removed condition attribute is a redundant condition attribute, and the redundant condition attribute is deleted to obtain the reduced condition attribute set and the reduced decision table.

S204: generating a decision tree model according to the reduced decision table.

Specifically, a decision coordination degree of each condition attribute in the reduced decision table is calculated, and a condition attribute with the greatest decision coordination degree is used as a root node.

Branches are determined according to the attribute values corresponding to the condition attributes in the reduced decision table, and the number of the branches is equal to the number of attribute values.

A condition determination degree of a corresponding attribute value on each branch is calculated.

If the condition determination degree is greater than or equal to the greatest decision coordination degree, a leaf node is generated under the branch corresponding to the corresponding attribute value; otherwise, a branch node is generated.

The condition attribute with the greatest decision coordination degree in the reduced decision table is deleted to obtain an updated decision table.

Using the branch node as a starting point, a root node and a branch are re-determined according to the updated decision table until all condition attributes in the decision table are determined as nodes, to obtain a decision tree model corresponding to the reduced decision table.

S205: generating a decision forest model according to at least one decision tree model.

Specifically, acquiring historical fault data of various fault types generated by various models, various versions, and various series of high-voltage generators; generating decision tree models respectively corresponding to various fault types according to the historical fault data of various fault types; determining a combination of all decision tree models as a decision forest model. A decision weight of each decision tree in the decision forest model is determined by the model, the version, and the series of the high voltage generator to be diagnosed.

S206: obtaining a fault type and a fault level corresponding to a fault of the high-voltage generator according to the decision forest model.

Specifically, each path in the decision forest model corresponds to a rule. Since the decision forest model is obtained through training according to historical fault data of various fault types generated by various models, various versions, and various series of high-voltage generators, when a piece of operation data of the high-voltage generator is input as an input variable to the decision forest model, the decision forest model can automatically identify the operation data and select a corresponding regular path to output a fault level corresponding to the fault of the high-voltage generator.

S207: determining an acceptable level of the fault according to the fault level and a frequency of occurrence of the same type of fault.

In some embodiments, the higher the fault level and the higher the frequency of occurrence of the same type of fault, it means that the more attention needs to be paid to the fault. Therefore, an acceptable level of the fault is obtained by combining the fault level and a frequency of occurrence of the same type of fault, so that the user takes a corresponding measure according to the acceptable level.

In this embodiment, according to the historical fault information and data, a rough set theory of data mining can be used to perform data pre-processing, remove the redundant attribute, and then the decision tree method is used to generate rules used for fault classification (i.e., the decision forest model). According to these rules, the data fed back from each high-voltage generator is discriminated and the fault data is classified, the type of actual or potential fault is identified, and based on this, a corresponding measure is taken and the user is prompted. This realizes early warning of the fault type and the level in advance, and can identify both an actual fault and a potential fault, improving the accuracy and timeliness of fault diagnosis.

Figure 3:
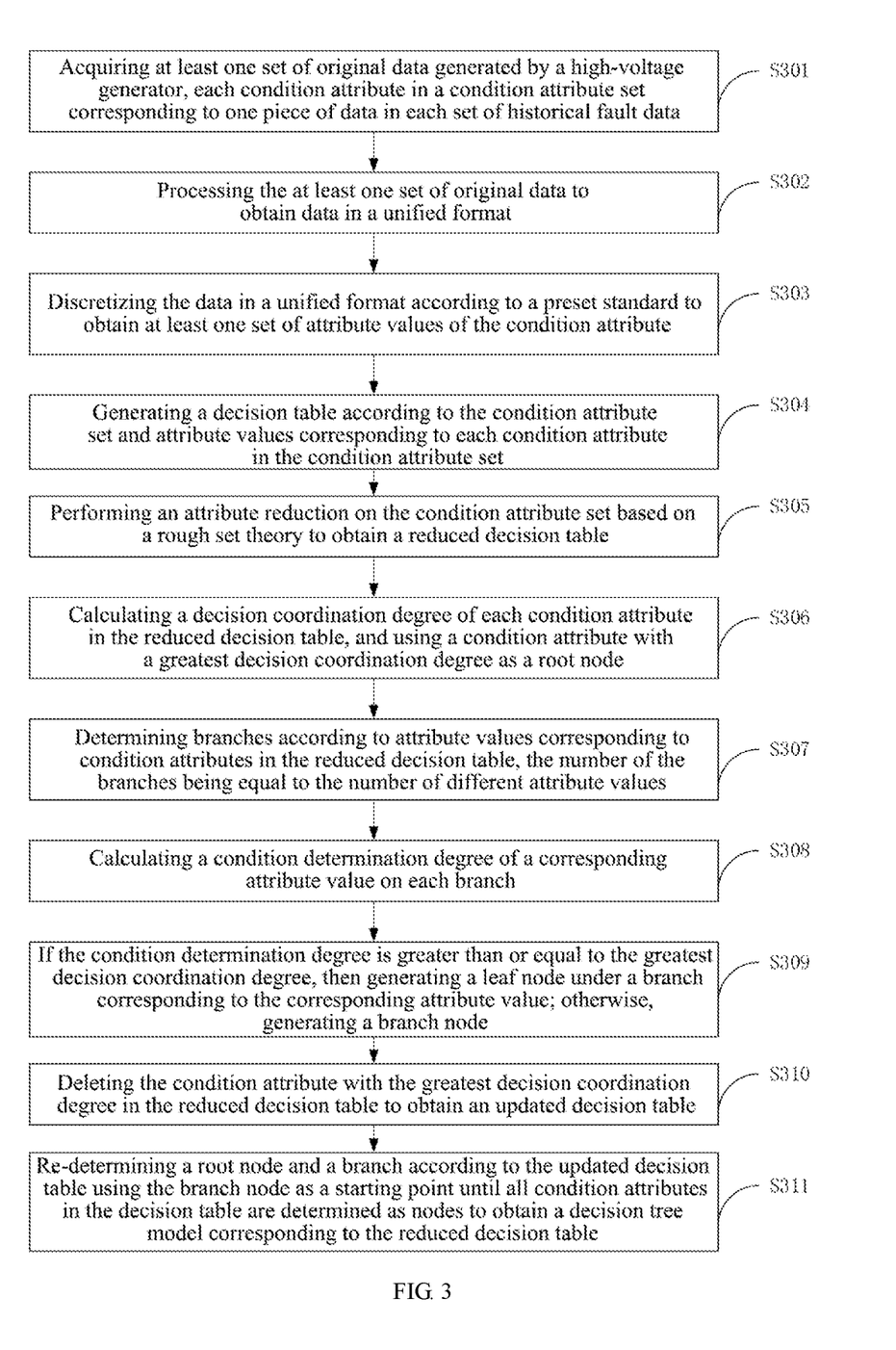
FIG. 3 is a schematic flowchart of a method for determining a decision tree model according to an exemplary embodiment of the present disclosure.

FIG. 3 is a schematic flowchart of a method for determining a decision tree model according to another exemplary embodiment of the present disclosure. This embodiment further describes an establishment process of the decision tree model in detail on the basis of the embodiment shown in FIG. 2.

As shown in FIG. 3, the method provided in this embodiment may include the following steps:

S301: acquiring at least one set of original data generated by the high-voltage generator, and each condition attribute in the condition attribute set corresponding to one piece of data in each set of original data.

S302: processing the at least one set of original data to obtain data in a unified format.

S303: discretizing the data in a unified format according to a preset standard to obtain at least one set of attribute values corresponding to the condition attribute set.

where the preset standard is shown in Table 1.

Specifically, referring to Table 1, each set of original data includes: exposure parameter, voltage and current curve, control parameter, tube current curve, filament current curve, temperature curve, error codes, and heat capacity HU.

TABLE 1

| Original data | Attribute conversion | Attribute content |
|---|---|---|
| Exposure parameter | a. Voltage | High(0) >= 100 kV<br>Medium(1)60-100 kV<br>Low(2) <= 60 kV |
|  | b. Current | Light load(0)(<=30 mA)<br>Medium load(1)(30-70 mA)<br>Heavy load(2)(>=70 mA) |
|  | c. Time | Long(0)(>=500 ms)<br>Medium(1)(100-500 ms)<br>Short(2)(<=100 ms) |
|  | d. Filament size | Large (0) Small (1) |
|  | e. Mode | Ms(0) mAs(1) |

TABLE 1-continued

| Original data | Attribute conversion | Attribute content |
|---|---|---|
| Voltage and current curve | f. Voltage overshoot | <1%(0) 1%-5%(1) >5%(2) |
| | g. Voltage drop | <1% (0) 1%-5%(1) >5%(2) |
| Control parameter | h. Steady state maximum frequency change | <5% (0) 5%-10%(1) >10%(2) |
| Tube current curve | i. Current overshoot | <1%(0) 1%-5%(1) >5%(2) |
| | j. Current drop | <1%(0) 1%-5%(1) >5%(2) |
| Filament current curve | k. Adjustment rate | <1%(0) 1%-5%(1) >5%(2) |
| Temperature curve | l. Maximum temperature change | <15%(0) 15%-30%(1) >30%(2) |
| Error code | m. Four-digit error code | 2003 (0) 2004 (1) 2007 (2) 3001 (3) 3002 (4) 3003 (5) 3006(6) 3007(7) |
| Heat capacity HU | n. Current HU | <15%(0) 15%-30%(1) >30%(2) |

Where one piece of data in each set of original data corresponds to one attribute in one condition attribute set. In one embodiment, the condition attribute set includes 14 condition attributes such as a voltage attribute (represented by a), a current attribute (represented by b), and a time attribute (represented by c). According to a value of each piece of original data in each set of original data, an attribute value of each condition attribute in a corresponding condition attribute set is determined. For example, a voltage in a first set of original data is 120 kilovolts (kV), then the attribute value corresponding the voltage attribute is 0; the current is 40 milliamps (mA), then the attribute value corresponding to the current attribute is 1; the maximum temperature change is 40%, then the attribute value corresponding to the temperature attribute is 2. Similarly, the attribute values corresponding to the condition attributes in each set of original data can be obtained by converting according to the attribute contents in Table 1.

S304: generating a decision table according to the condition attribute set and the attribute value corresponding to each condition attribute in the condition attribute set.

Specifically, the method in step S303 is used to obtain the condition attribute set of each set of original data, and the attribute values of the condition attributes in the condition attribute set are used to generate a decision table, as shown in Table 2.

TABLE 2

| | a | b | c | d | e | f | g | h | i | j | k | l | m | n | o |
|---|---|---|---|---|---|---|---|---|---|---|---|---|---|---|---|
| $u_1$ | 0 | 0 | 2 | 1 | 0 | 0 | 2 | 2 | 2 | 0 | 0 | 2 | 1 | 2 | 5 |
| $u_2$ | 0 | 2 | 1 | 1 | 1 | 0 | 2 | 2 | 2 | 0 | 0 | 1 | 1 | 2 | 1 |
| $u_3$ | 0 | 0 | 1 | 0 | 1 | 2 | 0 | 2 | 2 | 0 | 0 | 0 | 0 | 2 | 1 |
| $u_4$ | 1 | 1 | 2 | 0 | 0 | 2 | 2 | 2 | 0 | 0 | 0 | 0 | 5 | 0 | 3 |
| $u_5$ | 0 | 2 | 0 | 1 | 0 | 0 | 2 | 2 | 2 | 0 | 2 | 1 | 1 | 1 | 3 |
| $u_6$ | 0 | 2 | 1 | 1 | 1 | 0 | 2 | 2 | 2 | 0 | 0 | 1 | 1 | 1 | 1 |
| $u_7$ | 0 | 2 | 0 | 1 | 0 | 2 | 0 | 2 | 2 | 0 | 2 | 0 | 0 | 2 | 1 |
| ... | | | | | | | | | | | | | | | |

See Table 2, the decision table includes multiple pieces of original data (represented by $u_1, u_2 \ldots u_7 \ldots$), conditional attribute (represented by a, b, c ... n) corresponding to each piece of original data, and the attribute value corresponding to each condition attribute. Where o represents the decision attribute.

It should be noted that, for ease of description, this embodiment only lists condition attributes and attribute values corresponding to 7 pieces of original data. It can be understood that the original data is not limited to 7 pieces in a specific implementation.

S305: performing an attribute reduction on the condition attribute set based on a rough set theory to obtain a reduced decision table.

Specifically, an importance of the condition attribute set is calculated, one condition attribute in the condition attribute set is removed, and an importance of a remaining condition attribute set is calculated, and if the importance of the condition attribute set is the same as the importance of the remaining condition attribute set, then the removed condition attribute is a redundant condition attribute. Then the redundant condition attribute is deleted to get a reduced decision table.

The data in the decision table shown in Table 2 above is taken as an example, and the detailed description is as follows:

A set composed by 7 pieces of original data is determined as a discourse domain, and recorded as U, U={1,2,3,4,5,6,7}. All condition attribute sets are listed, and recorded as C, C={a, b, c, d, e, f, g, h, i, j, k, l, m, n}; a decision attribute set is record as D, D={o}. Then, indistinguishable relationships of both the condition attribute set and the decision attribute set are determined according to the attribute values in the condition attribute set and the attribute values in the decision attribute, and are respectively represented as U/ind (D) and U/ind (C), then U/ind (D)={(2,3,6,7), (4,5), (1)}, U/ind (C)={1,2,3,4,5,6,7}. Then a positive domain is calculated, and the positive domain is a set composed by elements in the condition attribute set C that can be fully attributed to the decision attribute D, and is recorded as $POS_C(D)$. In this embodiment, $POS_C(D)$={1,2,3,4,5,6,7}.

Firstly, an importance of the condition attribute set C is calculated and recorded as $\gamma_C(D)$, that is, a ratio of the number of elements in the positive domain to the number of elements in the discourse domain, and in this embodiment $\gamma_C(D)=7/7=1$.

Then, each condition attribute is removed in sequence to obtain a remaining condition attribute set, indistinguishable relationships the remaining condition attribute set and the decision attribute are listed, and a positive domain of the remaining condition attribute set and an importance of the remaining condition attribute set are calculated. For example, the condition attribute i is removed, then U/ind (C-i)={1,2,3,4,5,6,7}, $POS_{C-i}(D)$={1,2,3,4,5,6,7}, $\gamma_{C-i}(D)=7/7=1$; For another example, the condition attribute n is removed, then U/ind(C-n)={1,(2,6),3,4,5,7} $POS_{C-n}(D)$={1,3,4,5,7}, $\gamma_{C-n}(D)=5/7=0.7142$.

Finally, if the importance of the remaining condition attribute set remains unchanged after removing the condition attribute, then the removed condition attribute is a redundant condition attribute, and the redundant condition attribute can be reduced, i.e., deleted. For example, after removing the condition attribute i, the importance of the remaining condition attribute set is $\gamma_{(C-i)}(D)=1$, which is the same as the importance $\gamma_C(D)$ of the condition attribute set before the condition attribute i is removed. Therefore, i is a redundant condition attribute, and can be deleted. After removing the condition attribute n, the importance of the remaining condition attribute set is $\gamma_{(C-n)}(D)=0.7142$, which is different from $\gamma_C(D)$, then the condition attribute n cannot be reduced.

Similarly, according to the above reduction method, the decision table shown in Table 2 is reduced, and the resulting reduced decision table is as shown in Table 3.

TABLE 3

|       | a | c | g | n | o |
|-------|---|---|---|---|---|
| $u_1$ | 0 | 2 | 2 | 2 | 5 |
| $u_2$ | 0 | 1 | 2 | 2 | 1 |
| $u_3$ | 0 | 1 | 0 | 2 | 1 |
| $u_4$ | 1 | 2 | 2 | 0 | 3 |
| $u_5$ | 0 | 0 | 2 | 1 | 3 |
| $u_6$ | 0 | 1 | 2 | 1 | 1 |
| $u_7$ | 0 | 0 | 0 | 2 | 1 |
| ...   |   |   |   |   |   |

S306: calculating a decision coordination degree of each condition attribute in the reduced decision table, and using a condition attribute with a greatest decision coordination degree as a root node.

Figure 5:
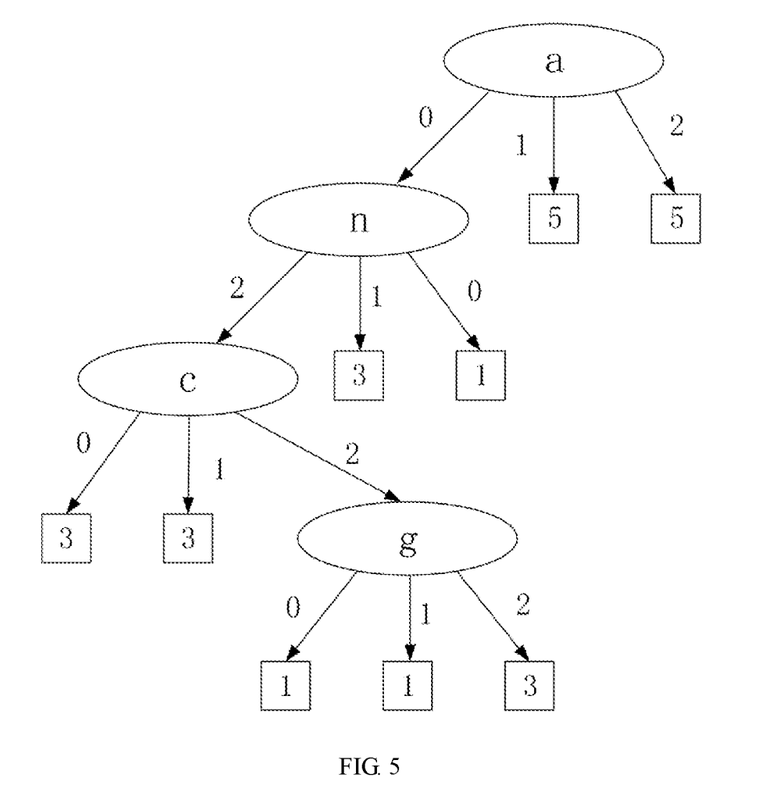
FIG. 5 is a schematic structural diagram of a decision tree model according to an exemplary embodiment of the present disclosure.

In conjunction with Table 2, the first 7 pieces of data is selected for the convenience of description, the condition attribute a is taken as an example to calculate the decision coordination degree of the condition attribute a (recorded as CON (a→o)). According to Table 2, U/ind (a)={(1,2,3,5,6,7), (4)}, the a value corresponding to (1,2,3,5,6,7) is 0, where the o value corresponding to 2, 3, 6, 7 is 1, the o value corresponding to 5 is 3, and the o value corresponding to 1 is 5. That is, when the corresponding a value is 0, there are 4 pieces of data corresponding to that the o value is 1, and there is 1 piece of data corresponding to that the o value is 3, there is 1 piece of data corresponding to that the o value is 5; the a value corresponding to (4) is 1, the corresponding o value is 3, and there is 1 piece of data. Then the decision coordination degree of condition attribute a is $$CON(a \rightarrow o) = \frac{4*4 + 1*1 + 1*1 + 1*1}{6*6 + 1*1} = 0.5135.$$

Where the numerator is obtained according to the number of piece of data with the same a value and the same o value, and the denominator is obtained according to the number of piece of data with the same a value. Similarly, for all data, respective decision coordination degrees of condition attributes a, c, g, and n are calculated respectively. After comparison, the decision coordination degree of the condition attribute a is the largest, CON(a→o)>CON(n→o)>CON (c→o)>CON(g→o), the greatest decision coordination degree of the condition attribute a is recorded as $CON_{max}$ (a→o), and the condition attribute a is determined as a root node, as shown in FIG. 5.

S307: determining branches according to attribute values corresponding to the condition attributes in the reduced decision table, the number of the branches being equal to the number of attribute values.

Specifically, the decision table is divided according to the attribute values at a current node, and each attribute value determines a branch. For example, in step 307, the condition attribute a is determined as the root node, and the root node is used as a starting point to determine the branch under the root node. As can be seen from Table 2, the reduced decision table includes three attribute values, which are 0, 1, and 2, respectively, then three branches are generated under the root node.

S308: calculating a condition determination degree of a corresponding attribute value on each branch.

S309: if the condition determination degree is greater than or equal to the greatest decision coordination degree, a leaf node is generated under the branch corresponding to the corresponding attribute value; otherwise, a branch node is generated.

For example, the condition determination degree corresponding to the attribute value is recorded as K(Ea$_i$), and the maximum decision coordination degree is $CON_{max}$(a→o) =0.6854.

When the attribute value corresponding to condition attribute a is 0, for the first 7 pieces of data, the corresponding condition determination degree is $$K(E(0)) = \frac{4*4 + 1*1 + 1*1}{6*6} = 0.5,$$

which is less than $CON_{max}$(a→o). Therefore, a branch node is generated under the branch corresponding to that the attribute value corresponding to the condition attribute a is 0. Similarly, the calculated condition determination degrees K(E(1)) and K(E(2)) corresponding to the calculated attribute values 1 and 2 are both greater than $CON_{max}$(a→o). Therefore, leaf nodes are generated under branches respectively corresponding to the attribute values 1 and 2, as shown in FIG. 5.

S310: deleting the condition attribute with the greatest decision coordination degree in the reduced decision table to obtain an updated decision table.

S311: re-determining a root node and a branch according to the updated decision table using the branch node as a starting point until all condition attributes in the decision table are determined as nodes to obtain a decision tree model corresponding to the reduced decision table.

Specifically, in each condition attribute in an updated decision table that does not include the condition attribute a, a condition attribute with the greatest decision coordination degree is selected. According to the description in step S306, it can be known that, in the remaining condition attributes, n has the greatest decision coordination degree. Therefore, the condition attribute n is determined as a node at the above-mentioned branch node.

Correspondingly, under the node corresponding to the condition attribute n, branches respectively corresponding to the attribute values 0, 1, and 2 are generated, and K(E(0)), K(E(1)), and K(E(2)) are compared with the decision coordination degree of the condition attribute n, a leaf node is generated under the branch corresponding to the attribute value when the condition determination degree of the attribute value greater than or equal to the decision coordination degree of the condition attribute n, a branch node is generated under the branch corresponding to the attribute value when the condition determination degree of the attribute value lower than the decision coordination degree of the condition attribute n.

Similarly, the root node and the branch are re-determined according to the updated decision table with the condition attribute n removed and taking a newly generated branch node as a starting point, until all condition attributes in the decision table are determined as nodes, and branches under the last attribute nodes all generate leaf nodes, and the resulting decision tree model is shown in FIG. 5.

Optionally, the method provided in this embodiment may further include: acquiring historical fault data of various fault types generated by various models, various versions, and various series of high-voltage generators; generating decision tree models respectively corresponding to various fault types according to the historical fault data of various fault types; determining a combination of all decision tree models as a decision forest model.

It should be noted that, for the steps that are not described in detail in this embodiment, reference may be made to the description of the method steps in the embodiment shown in FIG. 2, and details are not described here again.

In this embodiment, the historical fault data of the high-voltage generator is processed to generate a decision table, and then a decision tree model is established according to the decision table. Each path in the decision tree model corresponds to one rule. Further, all the historical fault data is divided into several data sets according to series, model and version of the high-voltage generator, and fault types. Each set contains a fixed number of data. One decision tree is generated for each set, and all decision tree models are combined into a decision forest model. Based on the decision forest model, actual and potential fault levels and types can be determined according to the operating data of the high-voltage generator.

Figure 4:
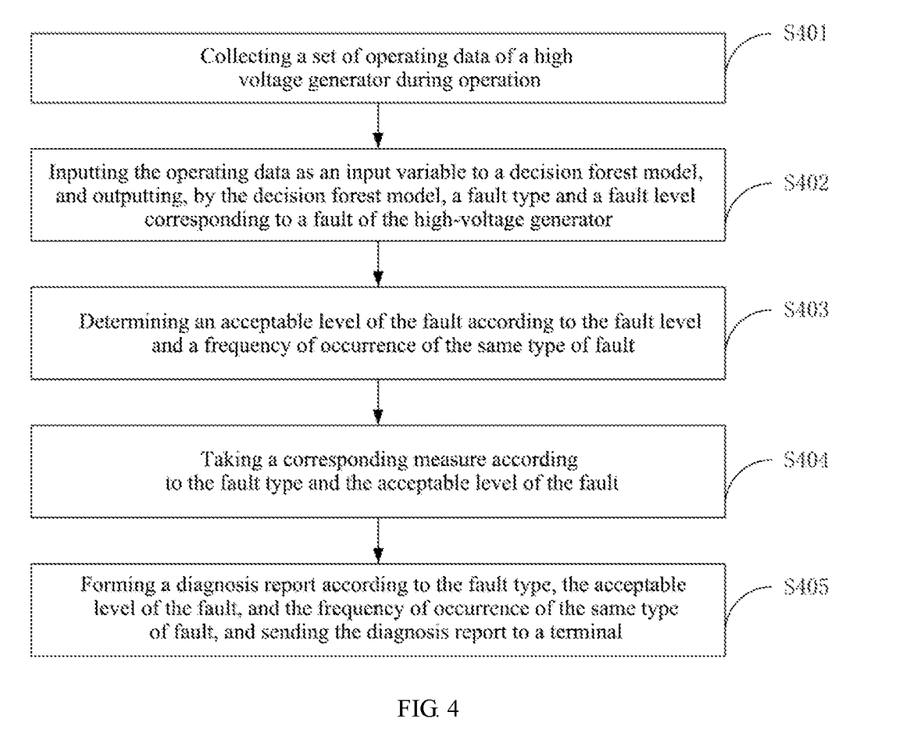
FIG. 4 is a schematic flowchart of a fault diagnosis method for a high-voltage generator according to another exemplary embodiment of the present disclosure.

FIG. 4 is a schematic flowchart of a fault diagnosis method for a high-voltage generator according to another exemplary embodiment of the present disclosure. This embodiment describes a fault diagnosis method for a high-voltage generator in detail on the basis of the embodiments shown in FIGS. 2 and 3.

As shown in FIG. 4, the method provided in this embodiment may include the following steps:

definition of each level is shown in Table 3. The fault level can also be divided into five levels, and a definition of each level is shown in Table 4.

TABLE 3

| Frequency level | | |
|---|---|---|
| Occurrence degree | Level | Definition |
| Often | 5 | Probability of occurrence exceeds $10^{-3}$, or the frequency of occurrence exceeds once a month |
| Possible | 4 | Probability of occurrence is between $10^{-4}$ and $10^{-3}$ or the frequency of occurrence is more than once every 3 months |
| Occasional | 3 | Probability of occurrence is between $10^{-5}$ and $10^{-4}$ or the frequency of occurrence exceeds once every 12 months |
| Very few | 2 | Probability of occurrence is between $10^{-6}$ and $10^{-5}$ or the frequency of occurrence exceeds once every 60 months |
| Impossible | 1 | Probability of occurrence is less than $10^{-6}$, basically impossible |

TABLE 4

| Fault level | | |
|---|---|---|
| Degree of Occurrence | Level | Definition |
| Catastrophic | 5 | Cause death or life-threatening serious injury, the loss exceeds $ 1,000,000 |
| Dangerous | 4 | Cause permanent partial disability, injury or occupational disease or causes at least three people to be hospitalized, the loss is between $ 200,000 and $ 1,000,000 |
| Severe | 3 | Causes work injury or occupational disease that requires a professional medical intervention, resulting in loss of one or more working days, the loss is between $ 10,000 and $ 200,000 |
| Minor | 2 | Causes temporary injury that does not require a professional medical intervention or disease that does not lose working days, the loss is between $ 2,000 and $ 10,000 |
| Negligible | 1 | Inconvenience or temporary discomfort, not requiring any medical treatment |

S401: collecting a set of operating data of the high voltage generator during operation.

S402: inputting the operating data as an input variable to the decision forest model, and outputting, by the decision forest model, a fault type and a fault level corresponding to a fault of the high-voltage generator.

In this step, the process of establishing the decision forest model may refer to the detailed description in the embodiment shown in FIG. 3.

S403: determining an acceptable level of the fault according to the fault level and a frequency of occurrence of the same type of fault.

Specifically, a frequency level is determined according to the frequency of occurrence of the same type of fault. The frequency level can be divided into five levels, and a Further, in combination with the contents in Tables 3 and 4, the acceptable level of the fault is determined according to the fault level and the frequency of occurrence of the same type of fault outputted by the decision forest model.

Where there are three acceptable levels, which are unacceptable level, re-evaluation level, and acceptable level, respectively.

For example, if the fault level is 5 and the frequency level is 5, then it is determined that the fault of the high voltage generator is the unacceptable level; and if the fault level is 1 and the frequency level is 1, then it is determined that the fault of the high voltage generator is the acceptable level. Specific determination rules are shown in Table 5.

TABLE 5

| Frequency level | Fault level | | | | |
|---|---|---|---|---|---|
| | 1 | 2 | 3 | 4 | 5 |
| 5 | Unacceptable | Unacceptable | Unacceptable | Unacceptable | Unacceptable |
| 4 | Re-evaluation | Unacceptable | Unacceptable | Unacceptable | Unacceptable |
| 3 | Acceptable | Re-evaluation | Unacceptable | Unacceptable | Unacceptable |
| 2 | Acceptable | Acceptable | Re-evaluation | Unacceptable | Unacceptable |
| 1 | Acceptable | Acceptable | Acceptable | Re-evaluation | Unacceptable |

S404: taking a corresponding measure according to the fault type and the acceptable level of the fault.

S405. forming a diagnosis report according to the fault type, the acceptable level of the fault, and the frequency of occurrence of the same type of fault, and sending the diagnosis report to a terminal.

Specifically, a diagnosis report is generated according to a result outputted by the decision forest. If it is determined to be the unacceptable level, the fault diagnosis system is locked and the maintenance personnel is notified; if it is determined to be the re-evaluation level, the fault diagnosis system continues to run; and if it is determined to be the acceptable level, the fault diagnosis system continues to run and issues a warning for prompting the user to pay attention to the usage method, and sends a diagnostic report to a display terminal to prompt the user.

In this embodiment, the data fed back from each high-voltage generator can be input into the established decision forest model in real time, to perform identification and classify the fault data, so as to identify a type of an actual or potential fault, find the cause of the fault based on this, and prompt the user.

Figure 6:
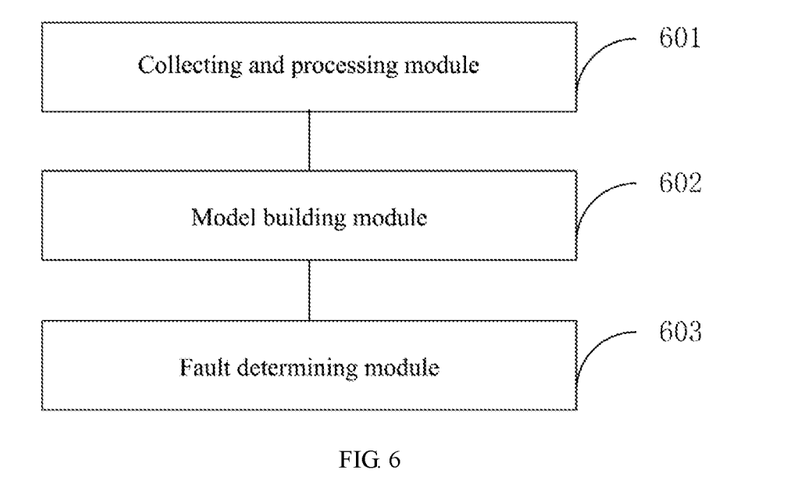
FIG. 6 is a schematic structural diagram of a fault diagnosis system for a high-voltage generator according to another exemplary embodiment of the present disclosure.

FIG. 6 is a schematic structural diagram of a fault diagnosis system for a high-voltage generator according to another exemplary embodiment of the present disclosure.

As shown in FIG. 6, the fault diagnosis system for the high-voltage generator provided in this embodiment includes: an collecting and processing module 601, a model building module 602, and a fault determining module 603; where the collecting and processing module 601 is configured to collect at least one set of original data of the high voltage generator during operation, pre-process the original data to obtain pre-processed data and generate a decision table, perform an attribute reduction based on the decision table to obtain a reduced decision table; the model building module 602 is configured to generate a decision tree model according to the reduced decision table, and generate a decision forest model according to at least one decision tree model; the fault determining module 603 is configured to obtain a fault type and a fault level corresponding to the fault of the high-voltage generator according to the decision forest model; the fault determining module is further configured to determine an acceptable level of the fault according to the fault level and a frequency of occurrence of the same type of fault.

Optionally, one piece of original data in each set of the original data corresponds to one condition attribute in a condition attribute set.

Optionally, the collecting and processing module 601 is specifically configured to: process the original data to obtain data in a unified format; discretize the data in a unified format according to a preset standard to obtain at least one set of attribute values of the condition attributes, the at least one set of attribute values corresponding to the at least one set of original data; generate the decision table according to the condition attributes and pre-processed data.

Optionally, the condition attribute set includes a plurality of condition attributes; the collecting and processing module 601 is specifically configured to: delete a redundant condition attribute to obtain a reduced decision table, calculate the importance of the condition attribute set, remove one condition attribute in the condition attribute set, and calculate the importance of the remaining condition attribute set, and if the importance of the condition attribute set is the same as the importance of the remaining condition attribute set, then the removed condition attribute being a redundant condition attribute.

Optionally, the model building module 602 is specifically configured to: calculate a decision coordination degree of each condition attribute in the reduced decision table, and use a condition attribute with a greatest decision coordination degree as a root node; determine branches according to the attribute values corresponding to the condition attribute in the reduced decision table, the number of the branches being equal to the number of attribute values; calculate a condition determination degree of a corresponding attribute value on each branch; if the condition determination degree is greater than or equal to the greatest decision coordination degree, generate a leaf node under a branch corresponding to a corresponding attribute value; otherwise, generate a branch node; delete the condition attribute with the greatest decision coordination degree in the reduced decision table to obtain an updated decision table; re-determine a root node and a branch according to the updated decision table using the branch node as a starting point until all condition attributes in the decision table are determined as nodes to obtain a decision tree model corresponding to the reduced decision table.

Optionally, the model building module 602 is further configured to: acquire historical fault data of various fault types generated by various models, various versions, and various series of high-voltage generators; generate decision tree models respectively corresponding to various fault types according to the historical fault data of various fault types; determine a combination of all the decision tree models as a decision forest model.

Optionally, the fault determining module 603 is further configured to: collect a set of operating data of the high voltage generator during operation; input the operating data as an input variable to the decision forest model, the decision forest model outputting a fault level corresponding to a fault of the high-voltage generator.

Optionally, the fault determining module 603 is further configured to take a corresponding measure according to the fault type and an acceptable level of the fault.

Optionally, the fault determining module 603 is further configured to form a diagnosis report according to the fault type, the acceptable level of the fault, and a frequency of occurrence of the same type of fault, and send the diagnosis report to a terminal.

Detailed function description of each module in this embodiment can refer to relevant the description in the embodiment of the method, and will not be described in detail here.

In an embodiment, a storage unit in the high-voltage converter may be a non-volatile memory, such as an erasable programmable read-only memory (EPROM), a flash.

Finally, it should be noted that the foregoing embodiments are merely intended to describe the technical solutions of the present disclosure rather than limit the present disclosure. Although the present disclosure is described in detail with reference to the foregoing embodiments, persons of ordinary skill in the art should understand that they may still make modifications to the technical solutions described in the foregoing embodiments, or make equivalent replacements to some or all technical features therein; these modifications or replacements do not cause the essence of corresponding technical solutions to depart from the scope of the technical solutions in the embodiments of the present disclosure.

What is claimed is:

1. A fault diagnosis method for a high-voltage generator, applied to a server, comprising:
   collecting at least one set of original data of the high voltage generator during operation;
   pre-processing the original data to obtain pre-processed data and generating a decision table;
   performing an attribute reduction based on the decision table to obtain a reduced decision table;
   generating a decision tree model according to the reduced decision table;
   generating a decision forest model according to at least one decision tree model;
   obtaining a fault type and a fault level corresponding to a fault of the high-voltage generator according to the decision forest model;
   determining an acceptable level of the fault according to the fault level and a frequency of occurrence of the same type of fault; and
   taking an early warning measure for the fault according to the fault type and the acceptable level of the fault;
   wherein the obtaining the fault type and the fault level corresponding to the fault of the high-voltage generator according to the decision forest model comprises:
   collecting a set of operating data of the high voltage generator during operation;
   inputting the operating data as an input variable to the decision forest model, and outputting, by the decision forest model, the fault type and the fault level corresponding to the fault of the high-voltage generator.

2. The method according to claim 1, wherein the collecting at least one set of original data of the high voltage generator during operation further comprises that one piece of original data in each set of the original data corresponds to one condition attribute in a condition attribute set.

3. The method according to claim 2, wherein the pre-processing the original data and generating the decision table comprises:
   processing the original data to obtain data in a unified format;
   discretizing the data in a unified format according to a preset standard to obtain at least one set of attribute values of the condition attribute, the at least one set of attribute values corresponding to the at least one set of original data; and
   generating the decision table according to the condition attribute and pre-processed data.

4. The method according to claim 3, wherein the condition attribute set comprises a plurality of condition attributes, performing the attribute reduction based on the decision table comprises:
   calculating an importance of the condition attribute set, removing one condition attribute in the condition attribute set, and calculating an importance of a remaining condition attribute set, and if the importance of the condition attribute set is the same as the importance of the remaining condition attribute set, then determining the removed condition attribute as a redundant condition attribute,
   deleting the redundant condition attribute to obtain the reduced decision table.

5. The method according to claim 4, wherein the generating the decision tree model according to the reduced decision table comprises:
   calculating a decision coordination degree of each condition attribute in the reduced decision table, and using a condition attribute with a greatest decision coordination degree as a root node;
   determining branches according to the attribute values corresponding to the condition attributes in the reduced decision table, with the number of the branches being equal to the number of the attribute values;
   calculating a condition determination degree of a corresponding attribute value on each branch;
   if the condition determination degree is greater than or equal to the greatest decision coordination degree, generating a leaf node under a branch corresponding to the corresponding attribute value; otherwise, generating a branch node;
   deleting the condition attribute with the greatest decision coordination degree in the reduced decision table, to obtain an updated decision table;
   re-determining a root node and a branch according to the updated decision table using the branch node as a starting point until all condition attributes in the decision table are determined as nodes, to obtain the decision tree model corresponding to the reduced decision table.

6. The method according to claim 1, further comprising:
   acquiring historical fault data of various fault types generated by various models, various versions, and various series of high-voltage generators;
   generating decision tree models respectively corresponding to different fault types according to the historical fault data of various fault types; and
   determining a combination of all decision tree models as the decision forest model.

7. The method according to claim 1, further comprising forming a diagnosis report according to the fault type, the acceptable level of the fault, and the frequency of occurrence of the same type of fault, and sending the diagnosis report to a terminal.

8. A fault diagnosis system for a high-voltage generator, comprising: a processor, and a memory for storing a computer program which, when executed by the processor, causes the processor to:
   collect at least one set of original data of the high voltage generator during operation, pre-process the original data to obtain pre-processed data and generate a decision table, perform an attribute reduction based on the decision table to obtain a reduced decision table;

generate a decision tree model according to the reduced decision table, and generate a decision forest model according to at least one decision tree model;

obtain a fault type and a fault level corresponding to a fault of the high-voltage generator according to the decision forest model;

determine an acceptable level of the fault according to the fault level and a frequency of occurrence of the same type of fault; and take an early warning measure for the fault according to the fault type and the acceptable level of the fault;

wherein the computer program specifically causes the processor to:

collect a set of operating data of the high voltage generator during operation;

input the operating data as an input variable to the decision forest model, and output, by the decision forest model, the fault type and the fault level corresponding to the fault of the high-voltage generator.

9. The fault diagnosis system for a high-voltage generator according to claim 8, wherein one piece of original data in each set of the original data corresponds to one condition attribute in a condition attribute set.

10. The fault diagnosis system for a high-voltage generator according to claim 9, wherein the computer program causes the processor to:

process the original data to obtain data in a unified format;

discretize the data in a unified format according to a preset standard, to obtain at least one set of attribute values of the condition attribute, the at least one set of attribute values corresponding to the at least one set of original data; and generate the decision table according to the condition attribute and the pre-processed data.

11. The fault diagnosis system for a high-voltage generator according to claim 10, wherein the condition attribute set comprises a plurality of condition attributes;

the computer program causes the processor to:

calculate an importance of the condition attribute set, remove one condition attribute in the condition attribute set, and calculate an importance of a remaining condition attribute set, and if the importance of the condition attribute set is the same as the importance of the remaining condition attribute set, then determine the removed condition attribute as a redundant condition attribute, delete the redundant condition attribute to obtain the reduced decision table.

12. The fault diagnosis system for a high-voltage generator according to claim 11, wherein the computer program causes the processor to:

calculate a decision coordination degree of each condition attribute in the reduced decision table, and use a condition attribute with a greatest decision coordination degree as a root node;

determine branches according to the attribute values corresponding to the condition attribute in the reduced decision table, the number of the branches being equal to the number of the attribute values;

calculate a condition determination degree of a corresponding attribute value on each branch;

if the condition determination degree is greater than or equal to the greatest decision coordination degree, generate a leaf node under a branch corresponding to the corresponding attribute value; otherwise, generate a branch node;

delete the condition attribute with the greatest decision coordination degree in the reduced decision table, to obtain an updated decision table;

re-determine, using the branch node as a starting point, a root node and a branch according to the updated decision table are determined, until all condition attributes in the decision table are determined as nodes, to obtain the decision tree model corresponding to the reduced decision table.

13. The fault diagnosis system for a high-voltage generator according to claim 8, wherein the computer program further causes the processor to:

acquire historical fault data of various fault types generated by various models, various versions, and various series of high-voltage generators;

generate decision tree models respectively corresponding to various fault types according to the historical fault data of various fault types; and determine a combination of all decision tree models as the decision forest model.

14. The fault diagnosis system for a high-voltage generator according to claim 8, wherein the computer program further causes the processor to form a diagnosis report according to the fault type, the acceptable level of the fault, and the frequency of occurrence of the same type of fault, and send the diagnosis report to a terminal.

* * * * *